United States Patent
Weber et al.

(10) Patent No.: US 7,904,132 B2
(45) Date of Patent: *Mar. 8, 2011

(54) SINE SATURATION TRANSFORM

(75) Inventors: Walter M. Weber, Laguna Hills, CA (US); Ammar Al-Ali, Tustin, CA (US); Lorenzo Cazzoli, Barcelona (ES)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/336,419

(22) Filed: Dec. 16, 2008

(65) Prior Publication Data

US 2009/0099429 A1     Apr. 16, 2009

Related U.S. Application Data

(63) Continuation of application No. 11/894,648, filed on Aug. 20, 2007, now Pat. No. 7,467,002, which is a continuation of application No. 11/417,914, filed on May 3, 2006, now Pat. No. 7,377,899, which is a continuation of application No. 11/048,232, filed on Feb. 1, 2005, now Pat. No. 7,373,194, which is a continuation of application No. 10/184,032, filed on Jun. 26, 2002, now Pat. No. 6,850,787.

(60) Provisional application No. 60/302,438, filed on Jun. 29, 2001.

(51) Int. Cl.
*A61B 5/1455* (2006.01)
*A61B 5/024* (2006.01)

(52) U.S. Cl. .......... 600/324; 600/323; 600/502; 702/190

(58) Field of Classification Search .................. 600/310, 600/322, 323, 324, 500, 502; 702/189, 190
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |

(Continued)

FOREIGN PATENT DOCUMENTS
WO    WO 98/42250    10/1998

(Continued)

*Primary Examiner* — Eric F Winakur
(74) *Attorney, Agent, or Firm* — Knobbe, Martens, Olson & Bear LLP

(57) ABSTRACT

A transform for determining a physiological measurement is disclosed. The transform determines a basis function index from a physiological signal obtained through a physiological sensor. A basis function waveform is generated based on basis function index. The basis function waveform is then used to determine an optimized basis function waveform. The optimized basis function waveform is used to calculate a physiological measurement.

20 Claims, 14 Drawing Sheets

U.S. PATENT DOCUMENTS

| | | |
|---|---|---|
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,853,364 A | 12/1998 | Baker et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,486 B1 | 2/2003 | Edgar et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |

| | | | | | | |
|---|---|---|---|---|---|---|
| 7,215,986 B2 | 5/2007 | Diab | | 7,341,559 B2 | 3/2008 | Schulz et al. |
| 7,221,971 B2 | 5/2007 | Diab | | 7,343,186 B2 | 3/2008 | Lamego et al. |
| 7,225,006 B2 | 5/2007 | Al-Ali et al. | | D566,282 S | 4/2008 | Al-Ali et al. |
| 7,225,007 B2 | 5/2007 | Al-Ali | | 7,355,512 B1 | 4/2008 | Al-Ali |
| RE39,672 E | 6/2007 | Shehada et al. | | 7,371,981 B2 | 5/2008 | Abdul-Hafiz |
| 7,239,905 B2 | 7/2007 | Kiani-Azarbayjany et al. | | 7,373,193 B2 | 5/2008 | Al-Ali et al. |
| 7,245,953 B1 | 7/2007 | Parker | | 7,373,194 B2 | 5/2008 | Weber et al. |
| 7,254,431 B2 | 8/2007 | Al-Ali | | 7,376,453 B1 | 5/2008 | Diab et al. |
| 7,254,433 B2 | 8/2007 | Diab et al. | | 7,377,794 B2 | 5/2008 | Al Ali et al. |
| 7,254,434 B2 | 8/2007 | Schulz et al. | | 7,377,899 B2 | 5/2008 | Weber et al. |
| 7,272,425 B2 | 9/2007 | Al-Ali | | 7,383,070 B2 | 6/2008 | Diab et al. |
| 7,274,955 B2 | 9/2007 | Kiani et al. | | 7,415,297 B2 | 8/2008 | Al-Ali et al. |
| D554,263 S | 10/2007 | Al-Ali | | 7,428,432 B2 | 9/2008 | Ali et al. |
| 7,280,858 B2 | 10/2007 | Al-Ali et al. | | 7,438,683 B2 | 10/2008 | Al-Ali et al. |
| 7,289,835 B2 | 10/2007 | Mansfield et al. | | 7,440,787 B2 | 10/2008 | Diab |
| 7,292,883 B2 | 11/2007 | De Felice et al. | | 7,454,240 B2 | 11/2008 | Diab |
| 7,295,866 B2 | 11/2007 | Al-Ali | | 7,467,002 B2 | 12/2008 | Weber |
| 7,328,053 B1 | 2/2008 | Diab et al. | | | | |
| 7,332,784 B2 | 2/2008 | Mills et al. | | | | |
| 7,340,287 B2 | 3/2008 | Mason et al. | | | | |

FOREIGN PATENT DOCUMENTS

WO  WO 02/047582 A3  6/2002

SINE SATURATION TRANSFORM

CROSS-REFERENCE TO RELATED APPLICATIONS

The present application claims priority benefit under 35 U.S.C. §120 to, and is a continuation of U.S. patent application Ser. No. 11/894,648, filed Aug. 20, 2007 entitled "Sine Saturation Transform," now U.S. Pat. No. 7,467,002 which is a continuation of U.S. patent application Ser. No. 11/417,914, filed May 3, 2006, entitled "Sine Saturation Transform," now U.S. Pat. No. 7,377,899, which is a continuation of, U.S. patent application Ser. No. 11/048,232, filed Feb. 1, 2005, entitled "Signal Component Processor," now U.S. Pat. No. 7,373,194 which is a continuation of U.S. patent application Ser. No. 10/184,032, filed Jun. 26, 2002, entitled "Signal Component Processor," now U.S. Pat. No. 6,850,787, which claims priority benefit under 35 U.S.C. §119(e) from U.S. Provisional Application No. 60/302,438, filed Jun. 29, 2001, entitled "Signal Component Processor." The present application also incorporates the foregoing disclosures herein by reference.

BACKGROUND OF THE INVENTION

Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximeter typically provides a numerical readout of the patient's oxygen saturation and pulse rate. A pulse oximetry system consists of a sensor attached to a patient, a monitor, and a cable connecting the sensor and monitor. Conventionally, a pulse oximetry sensor has both red (RD) and infrared (IR) light-emitting diode (LED) emitters and a photodiode detector. The pulse oximeter measurements are based upon the absorption by arterial blood of the two wavelengths emitted by the sensor. The pulse oximeter alternately activates the RD and IR sensor emitters and reads the resulting RD and IR sensor signals, i.e. the current generated by the photodiode in proportion to the detected RD and IR light intensity, in order to derive an arterial oxygen saturation value, as is well-known in the art. A pulse oximeter contains circuitry for controlling the sensor, processing the sensor signals and displaying the patient's oxygen saturation and pulse rate.

SUMMARY OF THE INVENTION

FIG. 1A illustrates a plethysmograph waveform 110, which is a display of blood volume, shown along the ordinate 101, over time, shown along the abscissa 102. The shape of the plethysmograph waveform 110 is a function of heart stroke volume, pressure gradient, arterial elasticity and peripheral resistance. Ideally, the waveform 110 displays a short, steep inflow phase 111 during ventricular systole followed by a typically three to four times longer outflow phase 112 during diastole. A dicrotic notch 116 is generally attributed to closure of the aortic valve at the end of ventricular systole.

FIG. 1B illustrates a corresponding RD or IR sensor signal s(t) 130, such as described above. The typical plethysmograph waveform 110 (FIG. 1A), being a function of blood volume, also provides a light absorption profile. A pulse oximeter, however, does not directly detect light absorption and, hence, does not directly measure the plethysmograph waveform 110. However, IR or RD sensor signals are 180° out-of-phase versions of the waveform 110. That is, peak detected intensity 134 occurs at minimum absorption 114 and minimum detected intensity 138 occurs at maximum absorption 118.

FIG. 1C illustrates the corresponding spectrum of s(t), which is a display of signal spectral magnitude $|S(\omega)|$, shown along the ordinate 105, versus frequency, shown along the abscissa 106. The plethysmograph spectrum is depicted under both high signal quality 150 and low signal quality 160 conditions. Low signal quality can result when a pulse oximeter sensor signal is distorted by motion-artifact and noise. Signal processing technologies such as described in U.S. Pat. No. 5,632,272, assigned to the assignee of the present invention and incorporated by reference herein, allow pulse oximetry to function through patient motion and other low signal quality conditions.

Ideally, plethysmograph energy is concentrated at the pulse rate frequency 172 and associated harmonics 174, 176. Accordingly, motion-artifact and noise may be reduced and pulse oximetry measurements improved by filtering out sensor signal frequencies that are not related to the pulse rate. Under low signal quality conditions, however, the frequency spectrum is corrupted and the pulse rate fundamental 152 and harmonics 154, 156 can be obscured or masked, resulting in errors in the computed pulse rate. In addition, a pulse rate, physiologically, is dynamic, potentially varying significantly between different measurement periods. Hence, maximum plethysmograph energy may not correspond to the computed pulse rate except under high signal quality conditions and stable pulse rates. Further, an oxygen saturation value calculated from an optical density ratio, such as a normalized red over infrared ratio, at the pulse rate frequency can be sensitive to computed pulse rate errors. In order to increase the robustness of oxygen saturation measurements, therefore, it is desirable to improve pulse rate based measurements by identifying sensor signal components that correspond to an optimization, such as maximum signal energy.

One aspect of a signal component processor comprises a physiological signal, a basis function index determined from the signal, a basis function waveform generated according to the index, a component derived from the sensor signal and the waveform, and a physiological measurement responsive to the component. In one embodiment, the component is responsive to the inner product of the sensor signal and the waveform. In another embodiment, the index is a frequency and the waveform is a sinusoid at the frequency. In that embodiment, the signal processor may further comprise a pulse rate estimate derived from the signal wherein the frequency is selected from a window including the pulse rate estimate. The physiological measurement may be an oxygen saturation value responsive to a magnitude of the component.

Another aspect of a signal component processor comprises a signal input, a basis function indicator derived from the signal input, a plurality of basis functions generated according to the indicator, a plurality of characteristics of the signal input corresponding to the basis functions and an optimization of the characteristics so as to identify at least one of said basis functions. In one embodiment, the indicator is a pulse rate estimate and the processor further comprises a window configured to include the pulse rate estimate, and a plurality of frequencies selected from within the window. In another embodiment, the characteristic comprises a plurality of signal remainders corresponding to the basis functions and a plurality of magnitudes of the signal remainders. In that embodiment, the optimization comprises a minima of the magnitudes. In a further embodiment, the characteristic comprises a plurality of components corresponding to the basis functions and a plurality of magnitudes of the components. In this embodiment, the optimization comprises a maxima of the magnitudes.

An aspect of a signal component processing method comprises the steps of receiving a sensor signal, calculating an estimated pulse rate, determining an optimization of the sensor signal proximate the estimated pulse rate, defining a frequency corresponding to the optimization, and outputting a physiological measurement responsive to a component of the sensor signal at the frequency. In one embodiment the determining step comprises the substeps of transforming the sensor signal to a frequency spectrum encompassing the estimated pulse rate and detecting an extrema of the spectrum indicative of the frequency. The transforming step may comprise the substeps of defining a window including the estimated pulse rate, defining a plurality of selected frequencies within the window, canceling the selected frequencies, individually, from the sensor signal to generate a plurality of remainder signals and calculating a plurality of magnitudes of the remainder signals. The detecting step may comprise the substep of locating a minima of the magnitudes.

In another embodiment, the outputting step comprises the substeps of inputting a red (RD) portion and an infrared (IR) portion of the sensor signal, deriving a RD component of the RD portion and an IR component of the IR portion corresponding to the frequency and computing an oxygen saturation based upon a magnitude ratio of the RD component and the IR component. The deriving step may comprise the substeps of generating a sinusoidal waveform at the frequency and selecting the RD component and the IR component utilizing the waveform. The selecting step may comprise the substep of calculating the inner product between the waveform and the RD portion and the inner product between the waveform and the IR portion. The selecting step may comprise the substeps of canceling the waveform from the RD portion and the IR portion, leaving a RD remainder and an IR remainder, and subtracting the RD remainder from the RD portion and the IR remainder from the IR portion.

A further aspect of a signal component processor comprises a first calculator means for deriving an optimization frequency from a pulse rate estimate input and a sensor signal, and a second calculator means for deriving a physiological measurement responsive to a sensor signal component at the frequency. In one embodiment, the first calculator means comprises a signal component transform means for determining a plurality of signal values corresponding to a plurality of selected frequencies within a window including the pulse rate estimate, and a detection means for determining a particular one of the selected frequencies corresponding to an optimization of the sensor signal. The second calculator means may comprise a waveform means for generating a sinusoidal signal at the frequency, a frequency selection means for determining a component of the sensor signal from the sinusoidal signal and a calculator means for deriving a ratio responsive to the component.

BRIEF DESCRIPTION OF THE DRAWINGS

FIG. 1A is a typical plethysmograph illustrating blood volume versus time;

FIG. 1B is a pulse oximetry sensor signal illustrating detected light intensity versus time;

FIG. 1C is a pulse oximetry sensor signal spectrum illustrating both high signal quality and low signal quality conditions;

FIG. 2 illustrates a frequency window around an estimated pulse rate; and

FIG. 3 illustrates an associated signal component transform;

FIG. 4 is a top-level functional block diagram of a signal component processor;

FIG. 5 is a functional block diagram of a frequency calculator;

FIG. 6 is a functional block diagram of a saturation calculator; and

FIG. 7 is a functional block diagram of one embodiment of a frequency selection;

FIG. 9 is a top-level functional block diagram of a signal component processor;

FIG. 10 is a functional block diagram of an index calculator; and

FIG. 11 is a functional block diagram of a measurement calculator.

DETAILED DESCRIPTION OF THE PREFERRED EMBODIMENTS

Figure 2:
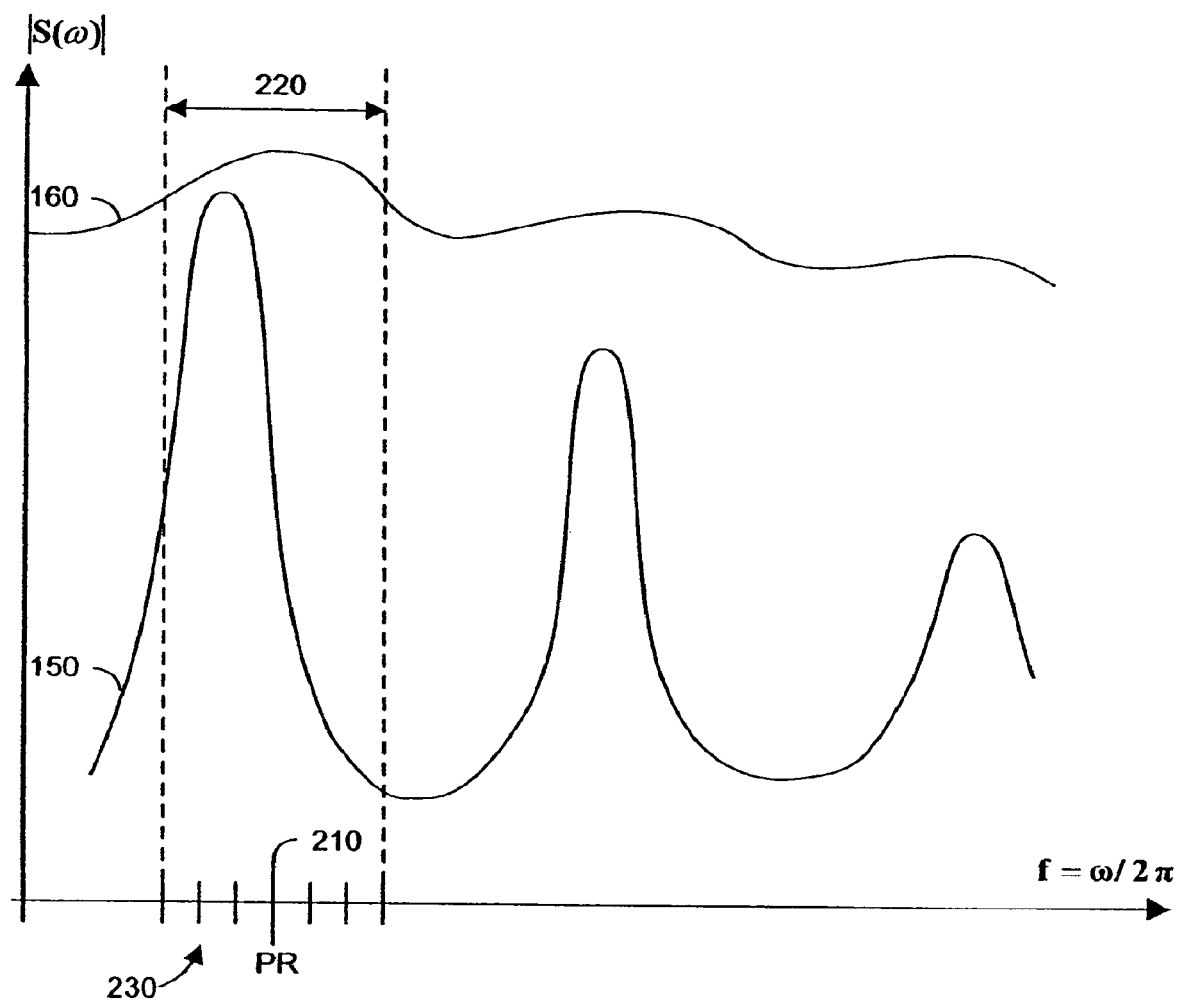
FIGS. 2-3 are magnitude versus frequency graphs for a pulse oximetry sensor signal illustrating an example of signal component processing.
Figure 3:
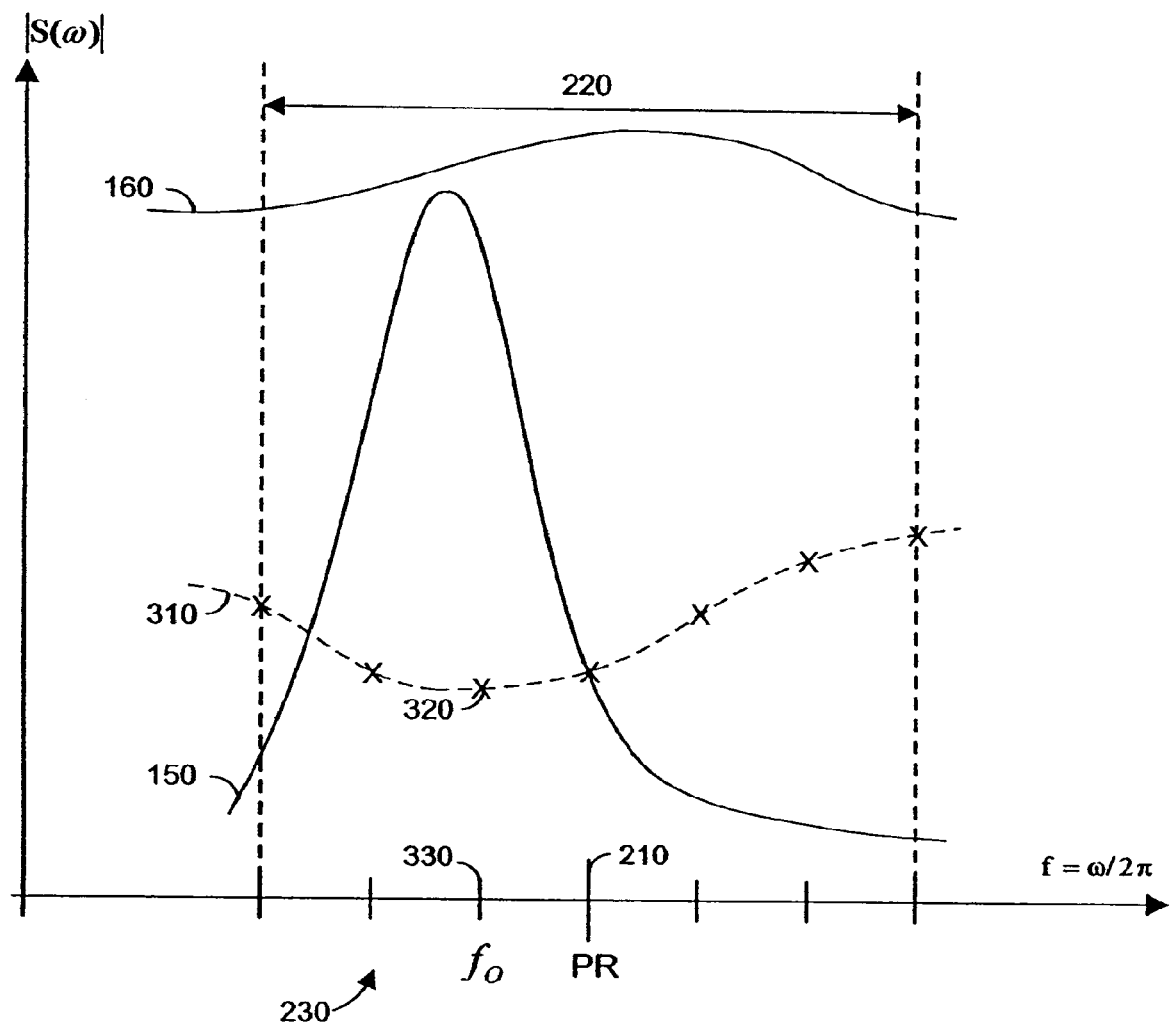

FIGS. 2 and 3 provide graphical illustration examples of signal component processing. Advantageously, signal component processing provides a direct method for the calculation of saturation based on pulse rate. For example, it is not necessary to compute a frequency transform, such as an FFT, which derives an entire frequency spectrum. Rather, signal component processing singles out specific signal components, as described in more detail below. Further, signal component processing advantageously provides a method of refinement for the calculation of saturation based on pulse rate.

Figure 1A:
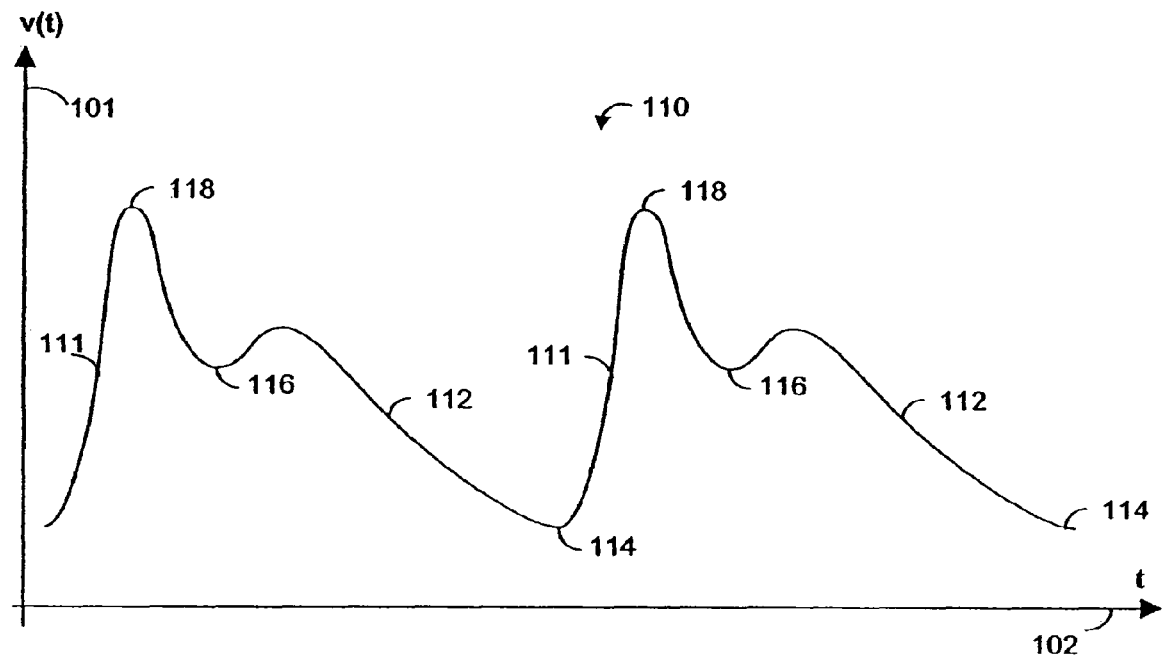
FIGS. 1A-C are graphical representations of a pulse oximetry sensor signal.
Figure 1B:
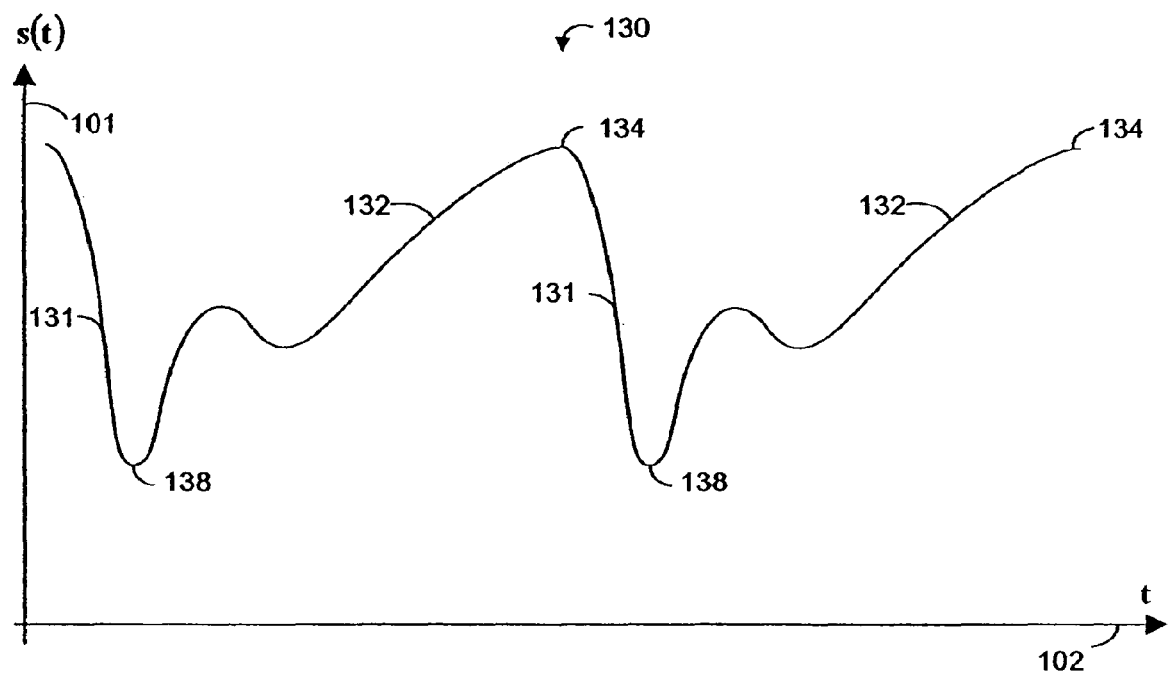
Figure 1C:
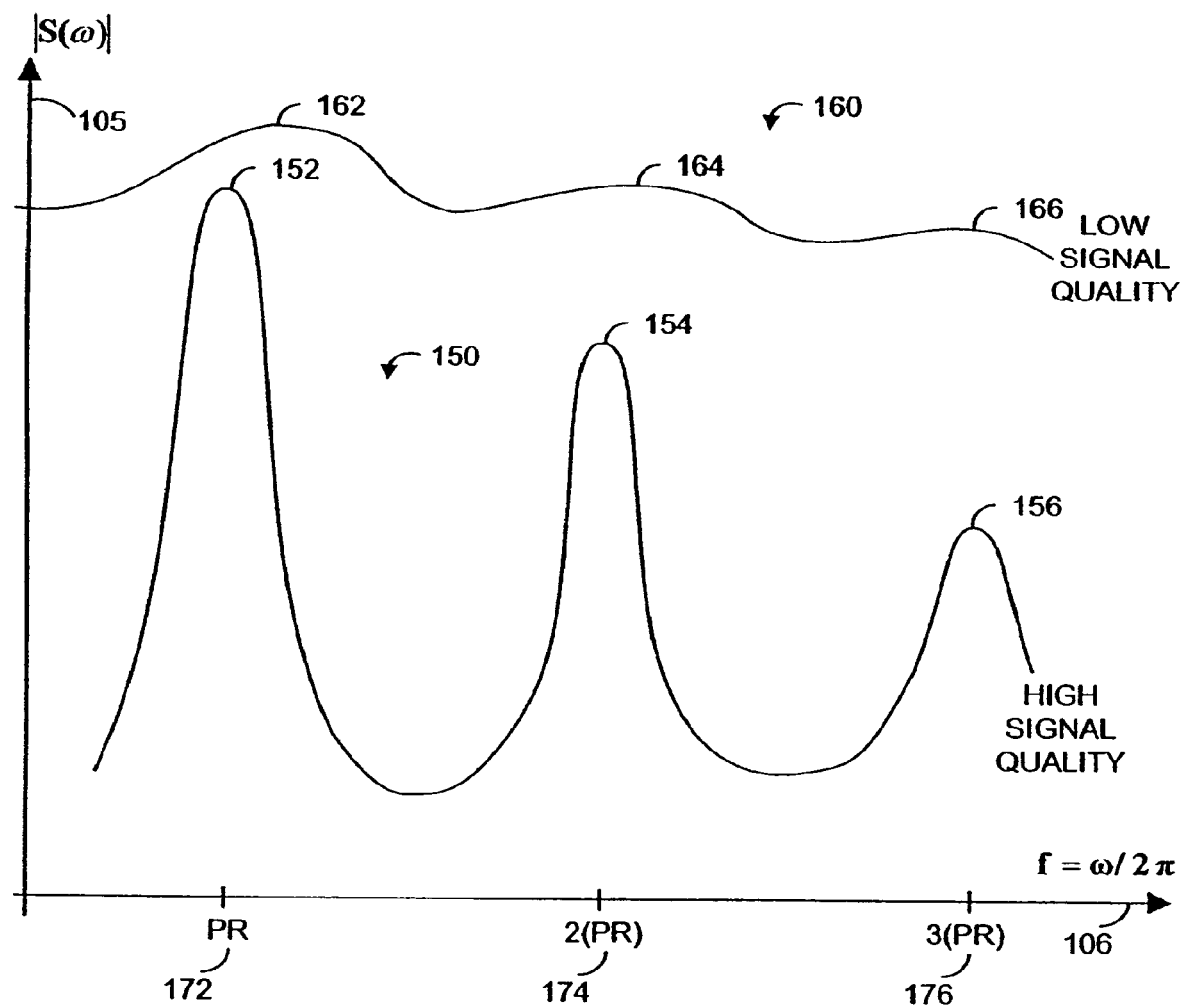

FIG. 2 illustrates high and low signal quality sensor signal spectrums 150, 160 as described with respect to FIG. 1C, above. A frequency window 220 is created, including a pulse rate estimate PR 210. A pulse rate estimate can be calculated as disclosed in U.S. Pat. No. 6,002,952, entitled "Signal Processing Apparatus and Method," assigned to the assignee of the present invention and incorporated by reference herein. A search is conducted within this window 220 for a component frequency $f_O$ at an optimization. In particular, selected frequencies 230, which include PR, are defined within the window 220. The components of a signal s(t) at each of these frequencies 230 are then examined for an optimization indicative of an extrema of energy, power or other signal characteristic. In an alternative embodiment, the components of the signal s(t) are examined for an optimization over a continuous range of frequencies within the window 220.

FIG. 3 illustrates an expanded portion of the graph described with respect to FIG. 2, above. Superimposed on the high signal quality 150 and low signal quality 160 spectrums is a signal component transform 310. In one embodiment, a signal component transform 310 is indicative of sensor signal energy and is calculated at selected signal frequencies 230 within the window 220. A signal component transform 310 has an extrema 320 that indicates, in this embodiment, energy optimization at a particular one 330 of the selected frequencies 230. The extrema 320 can be, for example, a maxima, minima or inflection point. In the embodiment illustrated, each point of the transform 310 is the magnitude of the signal remaining after canceling a sensor signal component at one of the selected frequencies. The extrema 320 is a minima, which indicates that canceling the corresponding frequency 330 removes the most signal energy. In an alternative embodiment, not illustrated, the transform 310 is calculated as the magnitude of signal components at each of the selected frequencies 230. In that embodiment, the extrema is a maxima, which indicates the largest energy signal at the corresponding frequency. The result of a signal component transform 310 is identification of a frequency $f_O$ 330 determined from the frequency of a signal component transform extrema 320. Frequency $f_O$ 330 is then used to calculate an oxygen saturation. A signal component transform and corresponding oxygen saturation calculations are described in additional detail with respect to FIGS. 4-8, below. Although signal component processing is described above with respect to identifying a particular frequency within a window including a pulse rate estimate PR, a similar procedure could be performed on 2PR, 3PR etc. resulting in the identification of multiple frequencies $f_{O1}$, $f_{O2}$, etc., which could be used for the calculation of oxygen saturation as well.

Advantageously, a signal component transform 310 is calculated over any set of selected frequencies, unrestricted by the number or spacing of these frequencies. In this manner, a signal component transform 310 differs from a FFT or other standard frequency transforms. For example, a FFT is limited to N evenly-distributed frequencies spaced at a resolution of $f_S/N$, where N is the number of signal samples and $f_S$ is the sampling frequency. That is, for a FFT, a relatively high sampling rate or a relatively large record length or both are needed to achieve a relatively high resolution in frequency. Signal component processing, as described herein, is not so limited. Further, a signal component transform 310 is advantageously calculated only over a range of frequencies of interest. A FFT or similar frequency transformation may be computationally more burdensome than signal component processing, in part because such a transform is computed over all frequencies within a range determined by the sampling frequency, $f_S$.

Figure 4:
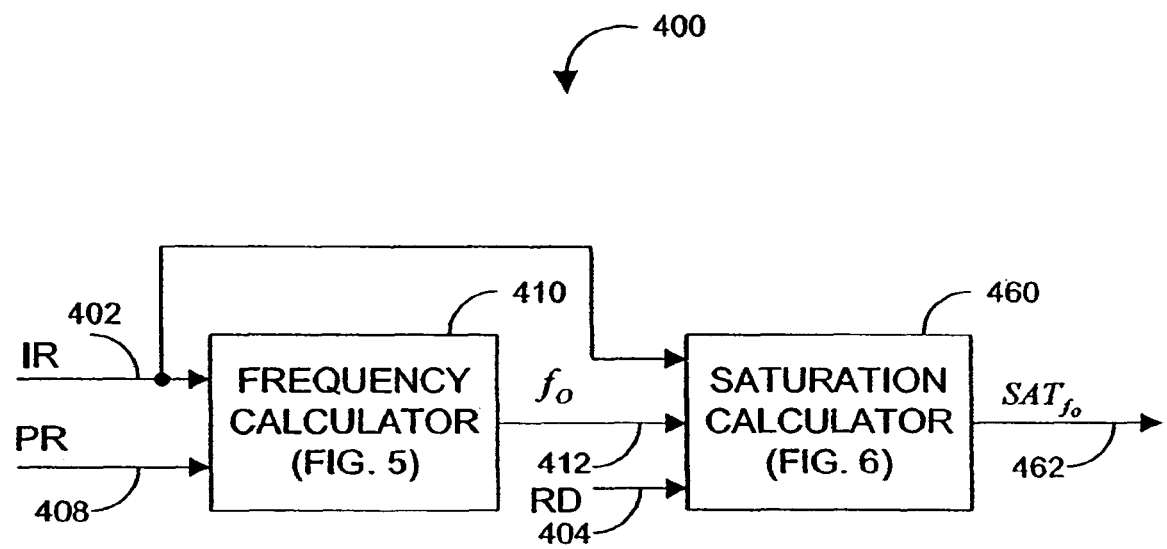
FIGS. 4-7 are functional block diagrams of one embodiment of a signal component processor.

FIGS. 4-7 illustrate one embodiment of a signal component processor. FIG. 4 is a top-level functional block diagram of a signal component processor 400. The signal component processor 400 has a frequency calculator 410 and a saturation calculator 460. The frequency calculator 410 has an IR signal input 402, a pulse rate estimate signal PR input 408 and a component frequency $f_O$ output 412. The frequency calculator 410 performs a signal component transform based upon the PR input 408 and determines the $f_O$ output 412, as described with respect to FIGS. 2-3, above. The frequency calculator 410 is described in further detail with respect to FIG. 5, below.

In an alternative embodiment, the frequency calculator 410 determines $f_O$ 412 based upon a RD signal input substituted for, or in addition to, the IR signal input 402. Similarly, one of ordinary skill in the art will recognize that $f_O$ can be determined by the frequency calculator 410 based upon one or more inputs responsive to a variety of sensor wavelengths.

The saturation calculator 460 has an IR signal input 402, a RD signal input 404, a component frequency $f_O$ input 412 and an oxygen saturation output, $SAT_{f_O}$ 462. The saturation calculator 460 determines values of the IR signal input 402 and the RD signal input 404 at the component frequency $f_O$ 412 and computes a ratio of those values to determine $SAT_{f_O}$ 462, as described with respect to FIG. 6, below. The IR signal input 402 and RD signal input 404 can be expressed as:

$$IR = \begin{bmatrix} IR_0 \\ \vdots \\ IR_{N-1} \end{bmatrix}; RD = \begin{bmatrix} RD_0 \\ \vdots \\ RD_{N-1} \end{bmatrix} \quad (1)$$

where N is the number of samples of each signal input.

Figure 5:
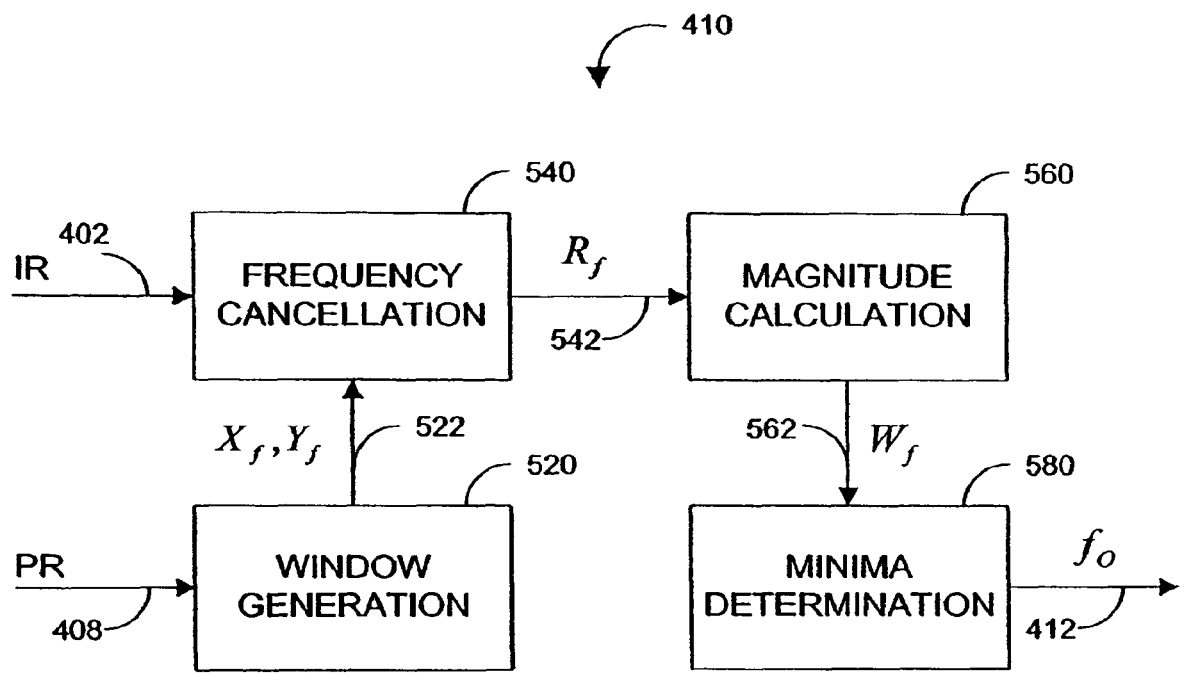

FIG. 5 shows one embodiment of the frequency calculator 410. In this particular embodiment, the frequency calculator functions are window generation 520, frequency cancellation 540, magnitude calculation 560 and minima determination 580. Window generation 520, frequency cancellation 540 and magnitude calculation 560 combine to create a signal component transform 310 (FIG. 3), as described with respect to FIG. 3, above. Minima determination 580 locates the signal component transform extrema 320 (FIG. 3), which identifies $f_O$ 412, also described with respect to FIG. 3, above.

As shown in FIG. 5, window generation 520 has a PR input 408 and defines a window 220 (FIG. 3) about PR 210 (FIG. 3) including a set of selected frequencies 230 (FIG. 3)

$$\{f_m; m = 0, \ldots M - 1\}; f = \begin{bmatrix} f_0 \\ \vdots \\ f_{M-1} \end{bmatrix} \quad (2)$$

where M is the number of selected frequencies 230 (FIG. 3) within the window 220 (FIG. 3). Window generation 520 has a sinusoidal output $X_f, Y_f$ 522, which is a set of sinusoidal waveforms $x_{n,f}, y_{n,f}$ each corresponding to one of the set of selected frequencies 230 (FIG. 3). Specifically $$X_f = \begin{bmatrix} x_{0,f} \\ \vdots \\ x_{N-1,f} \end{bmatrix}; Y_f = \begin{bmatrix} y_{0,f} \\ \vdots \\ y_{N-1,f} \end{bmatrix} \quad (3a)$$

$$x_{n,f} = \sin(2\pi fn); y_{n,f} = \cos(2\pi fn) \quad (4b)$$

Also shown in FIG. 5, the frequency cancellation 540 has IR 402 and $X_f, Y_f$ 522 inputs and a remainder output $R_f$ 542, which is a set of remainder signals $r_{n,f}$ each corresponding to one of the sinusoidal waveforms $x_{n,f}, y_{n,f}$. For each selected frequency f 230 (FIG. 3), frequency cancellation 540 cancels that frequency component from the input signal IR 402 to generate a remainder signal $r_{n,f}$. In particular, frequency cancellation 540 generates a remainder $R_f$ 542

$$R_f = \begin{bmatrix} r_{0,f} \\ \vdots \\ r_{N-1,f} \end{bmatrix} \quad (4a)$$

$$R_f = IR - \frac{IR \cdot X_f}{|X_f|^2} X_f - \frac{IR \cdot Y_f}{|Y_f|^2} Y_f \quad (4b)$$

Additionally, as shown in FIG. 5, the magnitude calculation 560 has a remainder input $R_f$ 542 and generates a magnitude output $W_f$ 562, where $$W_f = |R_f| = \sqrt{\sum_{n=0}^{N-1} r_{n,f}^2} \qquad (5)$$

Further shown in FIG. 5, the minima determination 580 has the magnitude values $W_f$ 562 as inputs and generates a component frequency $f_O$ output. Frequency $f_O$ is the particular frequency associated with the minimum magnitude value $$W_{f_O} = \min\{W_f\} \qquad (6)$$

Figure 6:
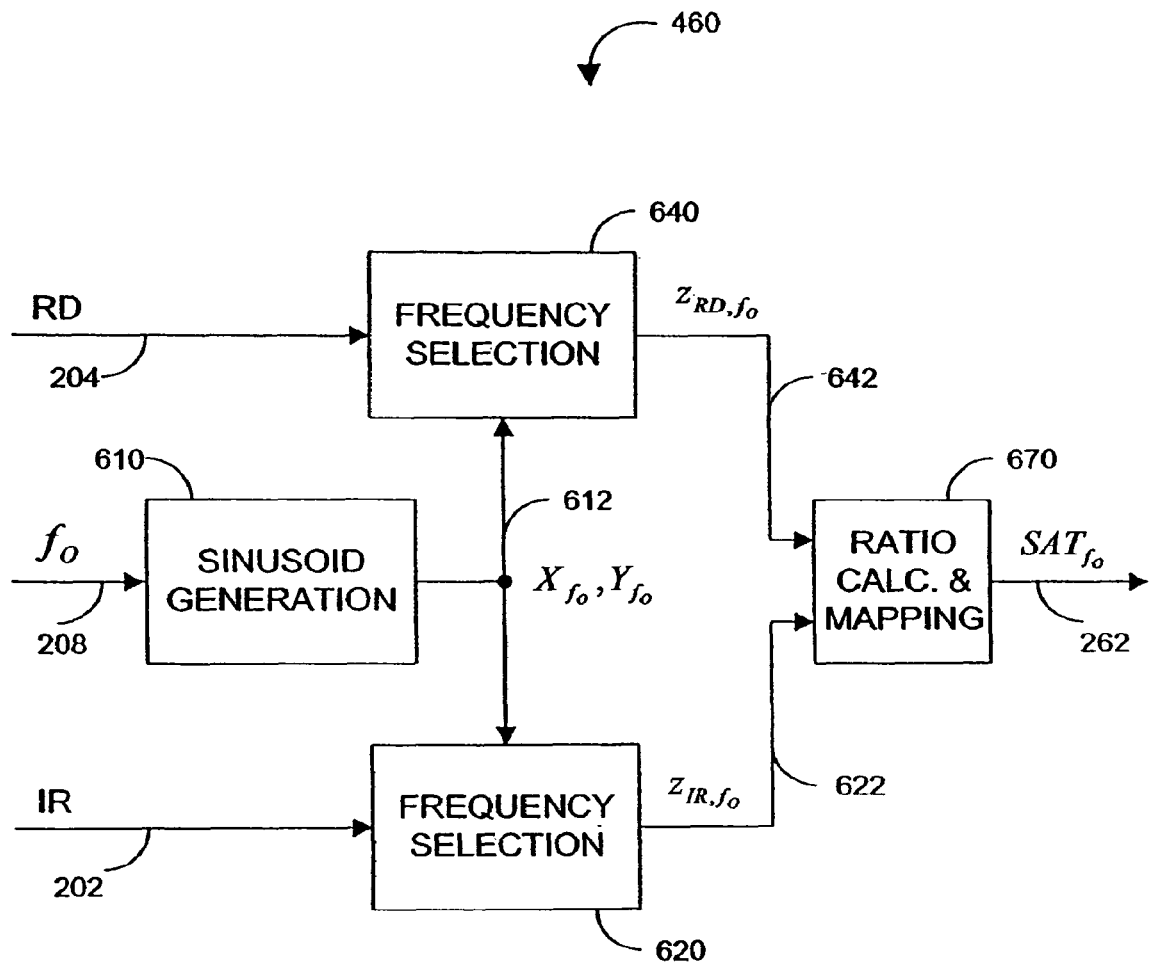

FIG. 6 shows that the saturation calculator 460 functions are sinusoid generation 610, frequency selection 620, 640 and ratio calculation 670. Sinusoid generation has a component frequency $f_O$ input 208 and a sinusoidal waveform $X_{f_O}$, $Y_{f_O}$ output 612, which has a frequency of $f_O$. Frequency selection 620, 640 has a sensor signal input, which is either an IR signal 202 or a RD signal 204 and a sinusoid waveform $X_{f_O}$, $Y_{f_O}$ input 612. Frequency selection 620, 640 provides magnitude outputs $Z_{IR,f_O}$ 622 and $Z_{RD,f_O}$ 642 which are the frequency components of the IR 202 and RD 204 sensor signals at the $f_O$ frequency. Specifically, from equation 3(a)

$$X_{f_O} = \begin{bmatrix} x_{0,f_O} \\ \vdots \\ x_{N-1,f_O} \end{bmatrix}; Y_{f_O} = \begin{bmatrix} y_{0,f_O} \\ \vdots \\ y_{N-1,f_O} \end{bmatrix} \qquad (7)$$

Then, referring to equation 1

$$z_{IR,f_O} = \left| \frac{IR \cdot X_{f_O}}{|X_{f_O}|^2} X_{f_O} + \frac{IR \cdot Y_{f_O}}{|Y_{f_O}|^2} Y_{f_O} \right| \qquad (8a)$$
$$= \sqrt{\frac{(IR \cdot X_{f_O})^2}{|X_{f_O}|^2} + \frac{(IR \cdot Y_{f_O})^2}{|Y_{f_O}|^2}}$$

$$z_{RD,f_O} = \left| \frac{RD \cdot X_{f_O}}{|X_{f_O}|^2} X_{f_O} + \frac{RD \cdot Y_{f_O}}{|Y_{f_O}|^2} Y_{f_O} \right| \qquad (8b)$$
$$= \sqrt{\frac{(RD \cdot X_{f_O})^2}{|X_{f_O}|^2} + \frac{(RD \cdot Y_{f_O})^2}{|Y_{f_O}|^2}}$$

For simplicity of illustration, EQS. 8a-b assume that the cross-product of $X_{f_O}$ and $Y_{f_O}$ is zero, although generally this is not the case. The ratio calculation and mapping 670 has $Z_{IR,f_O}$ 622 and $z_{RD,f_O}$ 642 as inputs and provides $SAT_{f_O}$ 262 as an output. That is $$SAT_{f_O} = g\{z_{RD,f_O} / z_{IR,f_O}\} \qquad (9)$$

where g is a mapping of the red-over-IR ratio to oxygen saturation, which may be an empirically derived lookup table, for example.

Figure 7:
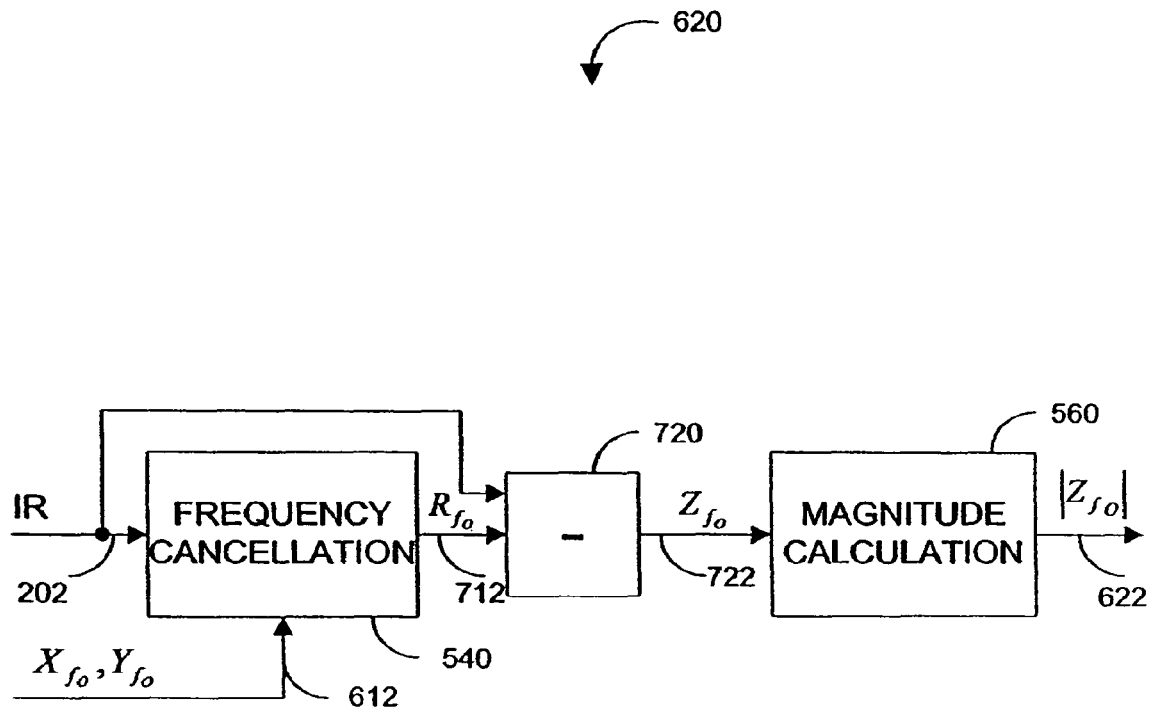

FIG. 7 illustrates an alternative embodiment of frequency selection 620 (FIG. 6), as described above. In this embodiment, frequency cancellation 540 and magnitude calculation 560, as described with respect to FIG. 5, can also be used, advantageously, to perform frequency selection. Specifically, frequency cancellation 540 has IR 202 and $X_{f_O}$, $Y_{f_O}$ 612 as inputs and generates a remainder signal $R_{f_O}$ 712 as an output, where $$R_{f_O} = IR - \frac{IR \cdot X_{f_O}}{|X_{f_O}|^2} X_{f_O} - \frac{IR \cdot Y_{f_O}}{|Y_{f_O}|^2} Y_{f_O} \qquad (10)$$

The remainder $R_{f_O}$ 712 is subtracted 720 from IR 202 to yield $$Z_{f_O} = IR - \left[ IR - \frac{IR \cdot X_{f_O}}{|X_{f_O}|^2} X_{f_O} - \frac{IR \cdot Y_{f_O}}{|Y_{f_O}|^2} Y_{f_O} \right] \qquad (11)$$
$$= \frac{IR \cdot X_{f_O}}{|X_{f_O}|^2} X_{f_O} + \frac{IR \cdot Y_{f_O}}{|Y_{f_O}|^2} Y_{f_O}$$

where $z_{f_O}$ 722 is the component of IR 202 at the $f_O$ frequency. The magnitude calculation 560 has $z_{f_O}$ 722 as an input and calculates $$|Z_{f_O}| = \left| \frac{IR \cdot X_{f_O}}{|X_{f_O}|^2} X_{f_O} + \frac{IR \cdot Y_{f_O}}{|Y_{f_O}|^2} Y_{f_O} \right| \qquad (12)$$
$$= \sqrt{\frac{(IR \cdot X_{f_O})^2}{|X_{f_O}|^2} + \frac{(IR \cdot Y_{f_O})^2}{|Y_{f_O}|^2}}$$

which is equivalent to equation 8a, above.

Figure 8A:
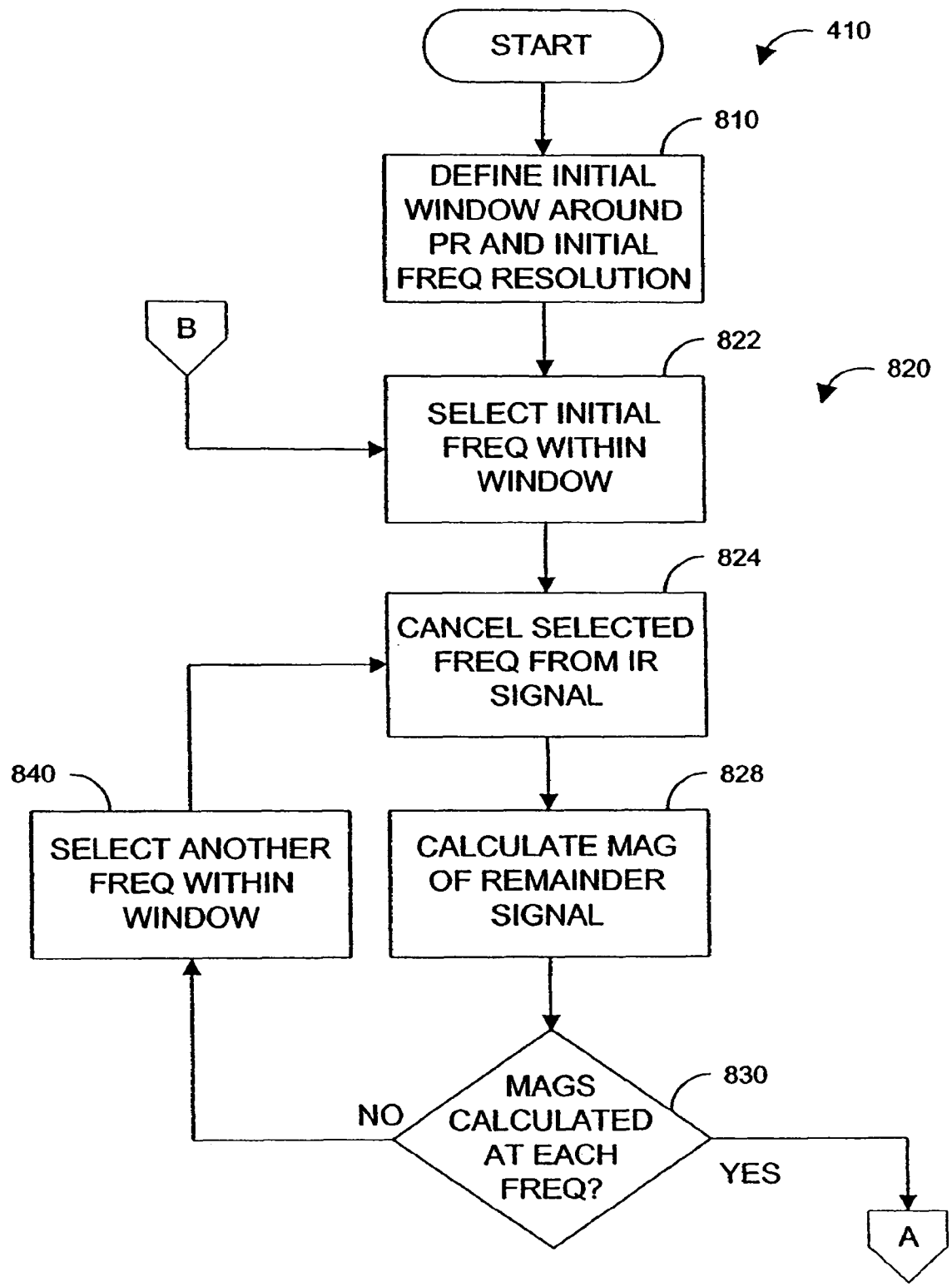
FIGS. 8A-B are flowcharts of an iterative embodiment of a frequency calculator.
Figure 8B:
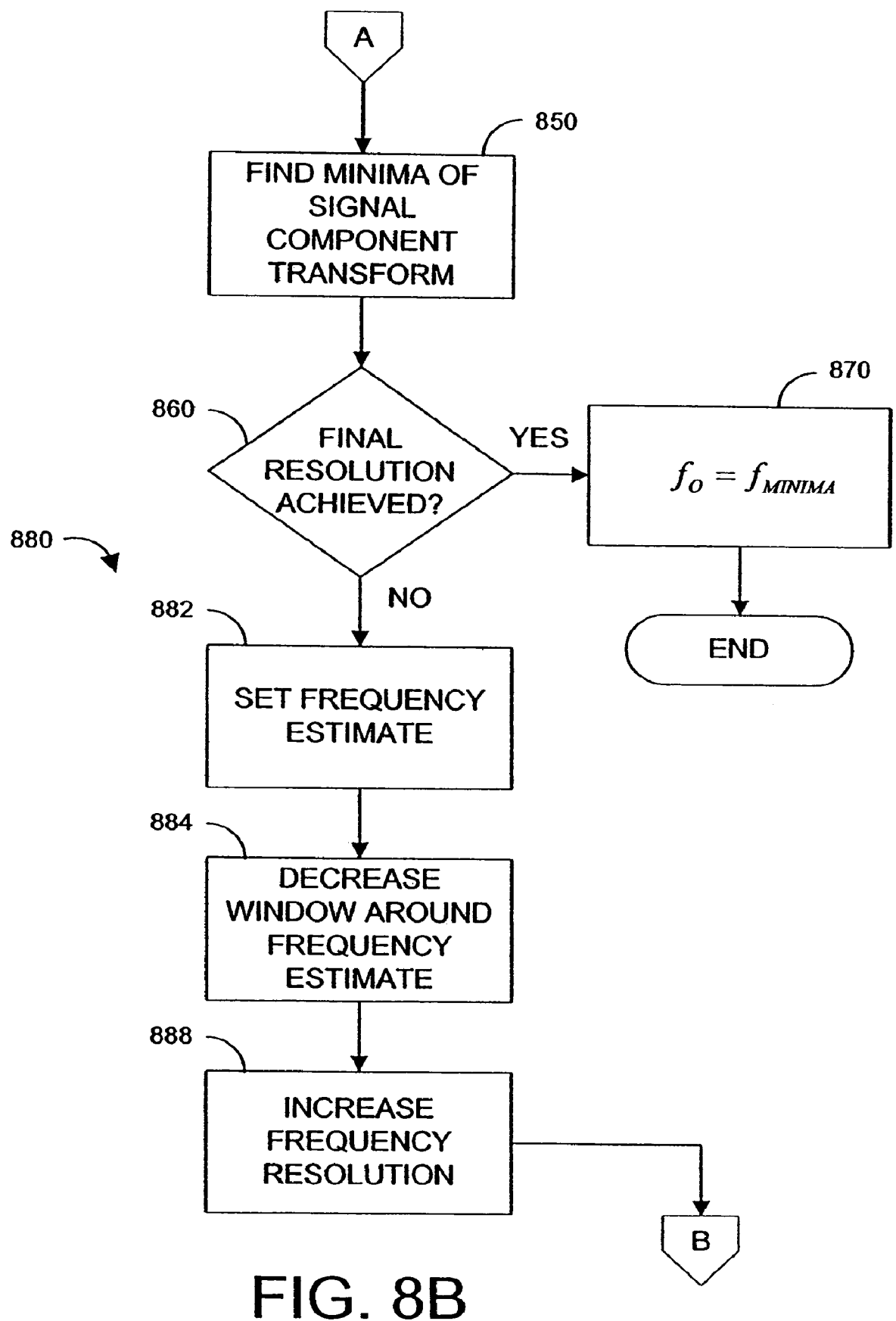

FIGS. 8A-B illustrate an iterative embodiment of the frequency calculator 410 (FIG. 4) described above. An iterative frequency calculator 410 has an initialization 810, a signal component transform 820, an extrema detection 850, a resolution decision 860 and a resolution refinement 880 and provides a component frequency $f_O$ 870. Initialization 810 defines a window around the pulse rate estimate PR and a frequency resolution within that window.

As shown in FIG. 8A, a signal component transform 820 has an initial frequency selection 822, a frequency cancellation 824 and an magnitude calculation 828. A decision block 830 determines if the magnitude calculation 828 has been performed at each frequency within the window. If not, the loop of frequency cancellation 824 and magnitude calculation 828 is repeated for another selected frequency in the window. The frequency cancellation 824 removes a frequency component from the IR sensor signal, as described with respect to FIG. 5, above. The magnitude calculation 828 determines the magnitude of the remainder signal, also described with respect to FIG. 5, above. If the decision block 830 determines that the remainder signal magnitudes have been calculated at each of the selected frequencies, then the signal component transform loop 820 is exited to the steps described with respect to FIG. 8B.

As shown in FIG. 8B, the extrema detector 850 finds a minima of a signal component transform 820 and a resolution decision block 860 determines if the final frequency resolution of a signal component transform is achieved. If not, resolution refinement 880 is performed. If the final resolution is achieved, the component frequency output $f_O$ is equated to the frequency of the minima 870, i.e. a signal component transform minima determined by the extrema detector 850.

Further shown in FIG. 8B, the resolution refinement 880 has a set frequency estimate 882, a window decrease 884 and a frequency resolution increase 888. Specifically, the frequency estimate 882 is set to a signal component transform minima, as determined by the extrema detector 850. The window decrease 884 defines a new and narrower window around the frequency estimate, and the frequency resolution increase 888 reduces the spacing of the selected frequencies within that window prior to the next iteration of a signal component transform 820. In this manner, a signal component transform 820 and the resulting frequency estimate are refined to a higher resolution with each iteration of signal component transform 820, extrema detection 850, and resolution refinement 880.

In a particular embodiment, the component calculation requires three iterations. A frequency resolution of 4 beats per minute or 4 BPM is used initially and a window of five or seven selected frequencies, including that of the initial pulse rate estimate PR, is defined. That is, a window of either 16 BPM or 24 BPM centered on PR is defined, and a signal component transform is computed for a set of 5 or 7 selected frequencies evenly spaced at 4 BPM. The result is a frequency estimate $f_1$. Next, the frequency resolution is reduced from 4 BPM to 2 BPM and a 4 BPM window centered on $f_1$ is defined with three selected frequencies, i.e. $f_1$−2 BPM, $f_1$, and $f_1$+2 BPM. The result is a higher resolution frequency estimate $f_2$. On the final iteration, the frequency resolution is reduced to 1 BPM and a 2 BPM window centered on $f_2$ is defined with three selected frequencies, i.e. $f_2$−1 BPM, $f_2$, and $f_2$+1 BPM. The final result is the component frequency $f_O$ determined by a signal component transform to within a 1 BPM resolution. This component frequency $f_O$ is then used to calculate the oxygen saturation, $SAT_{f_O}$, as described above.

The signal component processor has been described above with respect to pulse oximetry and oxygen saturation measurements based upon a frequency component that optimizes signal energy. The signal component processor, however, is applicable to other physiological measurements, such as blood glucose, carboxy-hemoglobin, respiration rate and blood pressure to name a few. Further, the signal component processor is generally applicable to identifying, selecting and processing any basis function signal components, of which single frequency components are one embodiment, as described in further detail with respect to FIG. 9, below.

Figure 9:
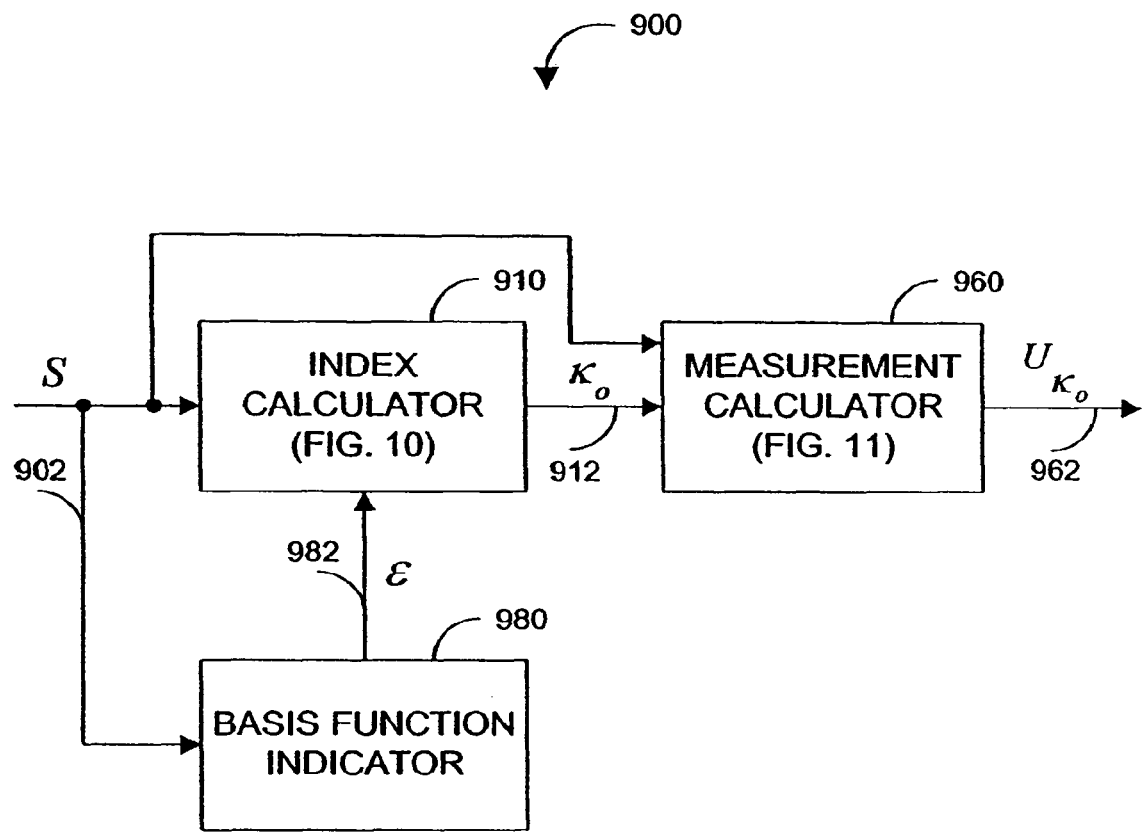
FIGS. 9-11 are functional block diagrams of another embodiment of a signal component processor.
Figure 10:
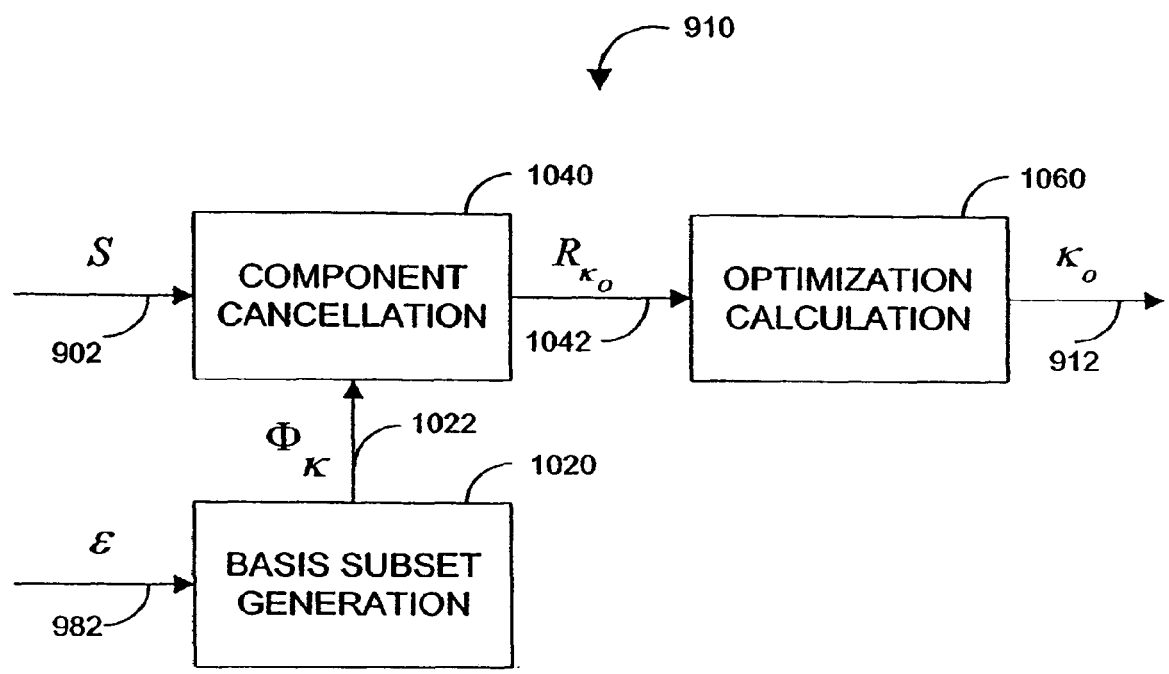
Figure 11:
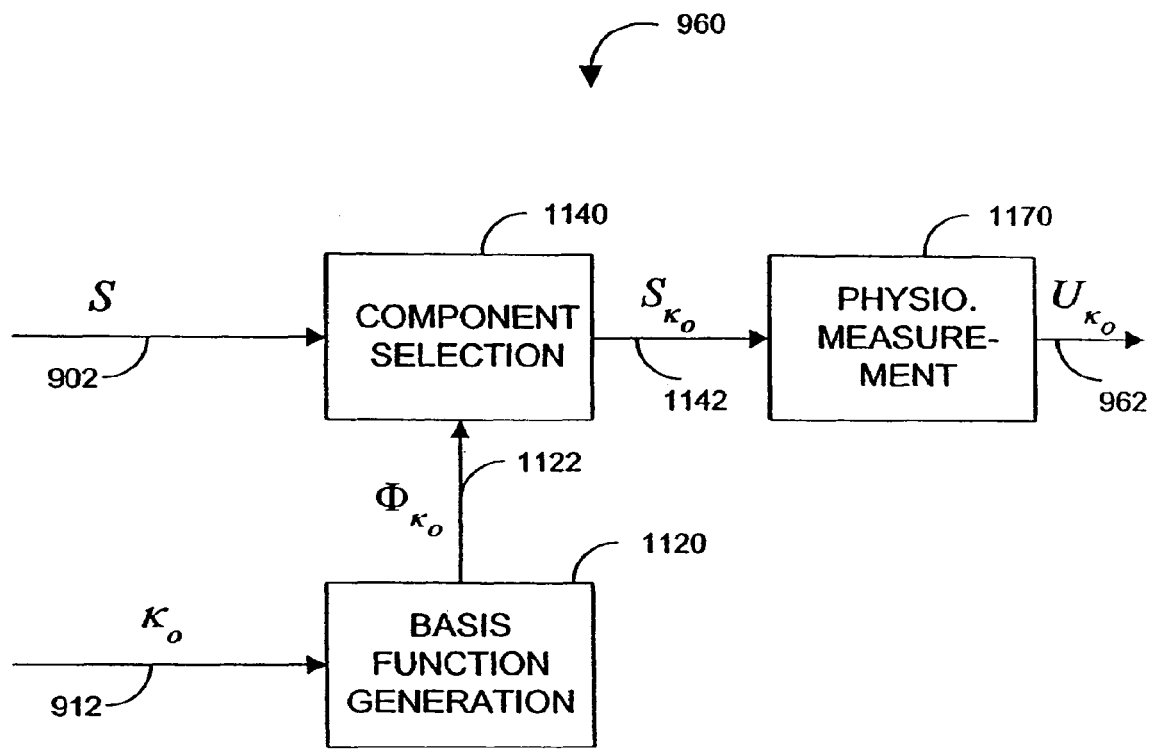

FIGS. 9-11 illustrate another embodiment of a signal component processor 900. As shown in FIG. 9, the processor 900 has an index calculator 910 and a measurement calculator 960. The index calculator has a sensor signal input S 902 and outputs a basis function index $\kappa_O$ 912, as described with respect to FIG. 10, below. The measurement calculator 960 inputs the basis function index $\kappa_O$ 912 and outputs a physiological measurement $U_{\kappa_O}$ 962, as described with respect to FIG. 11, below. The processor 900 also has a basis function indicator 980, which is responsive to the sensor signal input S 902 and provides a parameter ε 982 that indicates a set of basis functions to be utilized by the index calculator 910, as described with respect to FIG. 10, below.

As shown in FIG. 10, the functions of the index calculator 910 are basis subset generation 1020, component cancellation 1040 and optimization calculation 1060. The basis subset generation 1020 outputs a subset $\phi_\kappa$ 1022 of basis function waveforms corresponding to a set of selected basis function indices $\kappa$. The basis functions can be any complete set of functions such that $$S = \sum_\kappa a_\kappa \Phi_\kappa \quad (13)$$

For simplicity of illustration purposes, these basis functions are assumed to be orthogonal $$\langle \vec{\phi}_\gamma, \vec{\phi}_\eta \rangle = 0; \gamma \neq \eta \quad (14)$$

where $\langle \rangle$ = denotes an inner product. As such $$a_\kappa = \langle S, \phi_\kappa \rangle / \langle \phi_\kappa, \phi_\kappa \rangle = \quad (15)$$

$$S_\kappa = a_\kappa \phi_\kappa \quad (16)$$

In general, the basis functions may be non-orthogonal. The subset of basis functions generated is determined by an input parameter ε 982. In the embodiment described with respect to FIG. 5, above, the basis functions are sinusoids, the indices are the sinusoid frequencies and the input parameter ε 982 is a pulse rate estimate that determines a frequency window.

As shown in FIG. 10, the component cancellation 1040 generates a remainder output $R_\kappa$ 1042, which is a set of remainder signals corresponding to the subset of basis function waveforms $\phi_\kappa$ 1022. For each basis function waveform generated, component cancellation removes the corresponding basis function component from the sensor signal S 902 to generate a remainder signal. In an alternative embodiment, component cancellation 1040 is replaced with a component selection that generates a corresponding basis function component of the sensor signal S 902 for each basis function generated. The optimization calculation 1060 generates a particular index $\kappa_O$ 912 associated with an optimization of the remainders $R_\kappa$ 1042 or, alternatively, an optimization of the selected basis function signal components.

As shown in FIG. 11, the functions of the measurement calculator 960 are basis function generation 1120, component selection 1140, and physiological measurement calculation 1170. The component selection 1140 inputs the sensor signal S 902 and a particular basis function waveform $\phi_{\kappa_O}$ 1122 and outputs a sensor signal component $S_{\kappa_O}$ 1142. The physiological measurement 1170 inputs the sensor signal component $S_{\kappa_O}$ 1142 and outputs the physiological measurement $U_{\kappa_O}$ 962, which is responsive to the sensor signal component $S_{\kappa_O}$ 1142. In the embodiment described with respect to FIG. 6, above, the basis functions $\phi_\kappa$ are sinusoids and the index $\kappa_O$ is a particular sinusoid frequency. The basis function generation 1120 creates sine and cosine waveforms at this frequency. The component selection 1140 selects corresponding frequency components of the sensor signal portions, RD and IR. Also, the physiological measurement 1170 computes an oxygen saturation based upon a magnitude ratio of these RD and IR frequency components.

The signal component processor has been disclosed in detail in connection with various embodiments. These embodiments are disclosed by way of examples only and are not to limit the scope of the claims that follow. One of ordinary skill in the art will appreciate many variations and modifications.

What is claimed is:

1. In a patient monitor configured to obtain signals responsive to physiological parameters of a monitored patient, a method for filtering one or more of said signals to improve a determination of a pulse rate of the monitored patient, the method comprising:

receiving one or more signals indicative of light attenuated by body tissue of pulsing blood in said monitored patient, said one or more signals usable to determine physiological measurements and a pulse rate of said monitored patient;

electronically determining an initial frequency estimate of said pulse rate;

electronically combining at least one sinusoidal waveform responsive to said estimate of said pulse rate with said one or more of said signals to produce a predetermined signal response; and electronically signal component processing the combined signal to determine an output measurement of said pulse rate.

2. The method of claim 1, comprising sending said output measurement to a display.

3. The method of claim 2, comprising displaying said output measurement.

4. The method of claim 1, comprising generating one or more sinusoidal waves as the at least one sinusoidal waveform.

5. The method of claim 4, comprising individually canceling the generated sinusoidal waves from the one or more signals.

6. The method of claim 1, wherein said signal component processing includes determining a frequency corresponding to the sinusoidal waveform which produces an extrema.

7. The method of claim 6, wherein the extrema comprises a minima.

8. The method of claim 1, comprising segmenting the combined signal into at least one pulse rate cycle.

9. The method of claim 1, wherein said signal component processing includes determining an oxygen saturation.

10. The method of claim 1, wherein said initial frequency estimate of said pulse rate defines a window of selected frequencies.

11. The method of claim 10, wherein said at least one sinusoidal waveform is responsive to ones of said selected frequencies.

12. A patient monitor that obtains signals responsive to physiological parameters of a monitored patient and filters one or more of said signals to improve a determination of a pulse rate of the monitored patient, the monitor comprising:
   an input that receives (i) one or more signals indicative of light attenuated by body tissue of pulsing blood in said monitored patient, said one or more signals usable to determine physiological measurements and a pulse rate of said monitored patient, and (ii) an initial frequency estimate of said pulse rate; and
   a frequency calculator that combines at least one sinusoidal waveform responsive to said estimate of said pulse rate with said signals to produce a predetermined signal response, and signal component processes the combined signal to determine an output measurement of said pulse rate.

13. The patient monitor of claim 12, wherein the frequency calculator generates one or more sinusoidal waves as the at least one sinusoidal waveform.

14. The patient monitor of claim 13, wherein the frequency calculator individually cancels the generated sinusoidal waves from the one or more signals.

15. The patient monitor of claim 12, wherein the signal component processing done by the frequency calculator includes determining a frequency corresponding to the sinusoidal waveform which produces an extrema.

16. The patient monitor of claim 15, wherein the signal component processing done by the frequency calculator includes the extrema comprising a minima.

17. The patient monitor of claim 12, wherein the signal component processing done by the frequency calculator includes determining an oxygen saturation.

18. The patient monitor of claim 12, wherein the signal component processing done by the frequency calculator includes segmenting the combined signal into at least one pulse rate cycle.

19. The patient monitor of claim 12, wherein said initial frequency estimate of said pulse rate defines a window of selected frequencies.

20. The patient monitor of claim 19, wherein said at least one sinusoidal waveform is responsive to ones of said selected frequencies.

* * * * *

UNITED STATES PATENT AND TRADEMARK OFFICE
CERTIFICATE OF CORRECTION

PATENT NO. : 7,904,132 B2
APPLICATION NO. : 12/336419
DATED : March 8, 2011
INVENTOR(S) : Walter M. Weber et al.

It is certified that error appears in the above-identified patent and that said Letters Patent is hereby corrected as shown below:

At column 9, line 63, before "denotes" please delete "=".

At column 9, line 65, please delete "$\alpha_\kappa = \langle S, \phi_\kappa \rangle / \langle \phi_\kappa, \phi_\kappa \rangle =$" and insert therefore, -- $a_\kappa = \langle S, \Phi_\kappa \rangle / \langle \Phi_\kappa, \Phi_\kappa \rangle$ --.

At column 9, line 67, please delete "$S_\kappa = \alpha_\kappa \Phi_\kappa$" and insert therefore, -- $S_\kappa = a_\kappa \Phi_\kappa$ --.

Signed and Sealed this
Twenty-seventh Day of December, 2011

David J. Kappos
*Director of the United States Patent and Trademark Office*